United States Patent

Barzell et al.

(10) Patent No.: US 6,846,315 B2
(45) Date of Patent: Jan. 25, 2005

(54) TEMPLATE GRID

(75) Inventors: Winston E. Barzell, Sarasota, FL (US); Willet F. Whitmore, Sarasota, FL (US); Salvatore A. Uccello, Sarasota, FL (US); Roger F. Wilson, Sarasota, FL (US); Stephen E. Brauner, Bradenton, FL (US)

(73) Assignee: Barzell-Whitmore Maroon Bells, Inc., Sarasota, FL (US)

( * ) Notice: Subject to any disclaimer, the term of this patent is extended or adjusted under 35 U.S.C. 154(b) by 41 days.

(21) Appl. No.: 10/159,283

(22) Filed: Jun. 3, 2002

(65) Prior Publication Data

US 2002/0198514 A1 Dec. 26, 2002

Related U.S. Application Data

(60) Provisional application No. 60/294,555, filed on Jun. 1, 2001.

(51) Int. Cl.[7] .............................................. A61B 19/00
(52) U.S. Cl. ..................................................... 606/130
(58) Field of Search ........................ 606/130; 600/429; 128/635.2, 858

(56) References Cited

U.S. PATENT DOCUMENTS

| | | | |
|---|---|---|---|
| 3,508,552 A | 4/1970 | Hainault | 128/303 |
| 3,817,249 A | 6/1974 | Nicholson | 128/303 B |
| 4,167,179 A | 9/1979 | Kirsch | 128/1.2 |
| 4,402,308 A | 9/1983 | Scott | 128/1.2 |
| 4,427,005 A | 1/1984 | Tener | 128/303 R |
| 4,580,561 A | 4/1986 | Williamson | 128/303 B |
| 4,586,490 A | 5/1986 | Katz | 128/1.1 |
| 4,642,096 A | 2/1987 | Katz | 604/116 |
| 4,798,212 A | 1/1989 | Arana | 128/749 |
| 4,998,912 A | 3/1991 | Scarbrough et al. | 600/6 |
| 5,098,383 A | 3/1992 | Hemmy et al. | 604/116 |
| 5,242,373 A | 9/1993 | Scott et al. | 600/7 |
| 5,590,655 A * | 1/1997 | Hussman | 606/130 |
| 5,678,549 A | 10/1997 | Heywang-Koebrunner et al. | 606/130 |
| 5,681,327 A | 10/1997 | Heywang-Koebrunner | 606/130 |
| 5,702,405 A | 12/1997 | Heywang-Koebrunner | 606/130 |
| 5,769,779 A | 6/1998 | Alderson | 600/1 |
| 5,794,628 A * | 8/1998 | Dean | 606/130 |
| 6,036,632 A | 3/2000 | Whitmore, III et al. | 600/7 |
| 6,159,221 A * | 12/2000 | Chakeres | 606/130 |

OTHER PUBLICATIONS

Martinez, A., M.D. et al., "A Multiple–Site Perineal Applicator (MUPIT) For Treatment of Prostatic, Anorectal, and Gynecologic Malignancies," International Journal of Radiation, Oncology, Biology and Physiology Technical Innovations and Notes, 10(2):1–9, Feb. 1984.

* cited by examiner

Primary Examiner—Kevin T. Truong
(74) Attorney, Agent, or Firm—Merchant & Gould P.C.

(57) ABSTRACT

The present invention relates to a medical device guide, such as a template guide. The device guide includes a frame a frame having a plurality of network supports. A wire network is supported by the network supports thereby forming a plurality of meshes. A medical device may be inserted through one of the meshes to guide a position of the medical device.

5 Claims, 1 Drawing Sheet

TEMPLATE GRID

RELATED APPLICATIONS

This application claims the benefit of provisional application No. 60/294,555, filed Jun. 1, 2001, which application is incorporated by reference herein.

FIELD OF THE INVENTION

This invention relates generally to a template grid for positioning medical implants, and more particularly to a template grid for use with transrectal ultrasound imaging probes in brachytherapy for cancerous prostate and related surgeries.

BACKGROUND OF THE INVENTION

There are a number of treatments that require a transperineal guidance systems. For example, brachytherapy is performed with the patient in the lithotomy position, using an ultrasound imaging probe placed in the rectum to monitor seed placement. A template grid arrangement, which is kept in precise linear orientation with the ultrasound probe, must be accurately oriented adjacent the perineum in relation to the prostate, and locked in position throughout the procedure to achieve optimum seed placement. Precise and reproducible orientation and positioning of the ultrasound imaging probe in the rectum is a key element in both the calculations required for determining the number and distribution of radioactive seeds required for treatment and their subsequent placement using preloaded needles guided by the perineal template and real time ultrasound imaging. Even with proper probe positioning, placement of the seed-delivering needles using the template grid needs to be accurate and precisely coordinated with the images from the probe and the patient's anatomy to have effective therapy.

One commonly available template grid used to guide placement of the needles is a relatively thick block (approximately 2 cm in thickness) of plastic or metal with multiple machined parallel holes arranged in a matrix and spaced at 5 mm intervals. An example of such a template grid is the needle guidance template used with the ULTRA-STEP™ stepping device available from Civco Medical Instruments of Kalona, Iowa. The template grid needs to be thick to have accurate needle placement by ensuring the needle is inserted perpendicular to the face of the template grid. As these block template grids are reused on different patients, one area of potential risk is microbial cross-contamination. Although the template grids are chemically and physically washed and then sterilized between uses, the geometry and small size of the needle holes in the matrix makes reliable sterilization extremely difficult. As the cleaning and sterilization procedures can be quite time consuming, a reusable template grid has a significant amount of "down time" during which it cannot be used.

Disposable template grids, which essentially eliminate the possibility of cross-contamination and the other problems associated with reusable grids, are commercially available. One design uses a series of thin plates held in parallel and aligned by welded or machined brackets. One example of such a design is the template available with the brachytherapy ultrasound system sold by Carolina Medical Inc. of King, N.C. Spacing the plates apart from each other ensures that the needles are inserted perpendicular to the face of the template grid. The multi-plate design does make cleaning and sterilization less problematic and also eliminates some of the manufacturing difficulties of the thick block design. The down time due to cleaning and sterilization, however, remains essentially unaffected. Furthermore, the manufacturing costs involved in accurately and securely aligning, spacing, and joining the plates make producing a disposable multi-plate template grid unrealistic. Another design, disclosed in U.S. Pat. No. 6,036,632, is an injection-molded completely disposable template grid. A template grid that used less disposable material or disposable material that is available at a lower cost than injection-molded material would be advantageous.

Thus, there exists a need for an improved template grid.

SUMMARY OF THE INVENTION

One aspect of the present invention relates to a medical device guide. In one embodiment the medical device guide may be used to guide a medical device, such as a needle, for positioning a radioactive seed with respect to a prostate of an individual. The medical device guide comprises a frame having a plurality of network supports. A wire network may be supported from the network supports to define a plurality of meshes, which are openings or interstices between a wire of the network. By "wire" it is meant something resembling a wire, such as a suture, strand, filament, thread, or similar slender material. The medical device may be inserted through one of the meshes to thereby assist guidance of the medical device.

DESCRIPTION OF THE DRAWINGS

The present invention is discussed below in relation to the drawings in which.

DESCRIPTION OF THE PRESENT INVENTION

Figure 1:
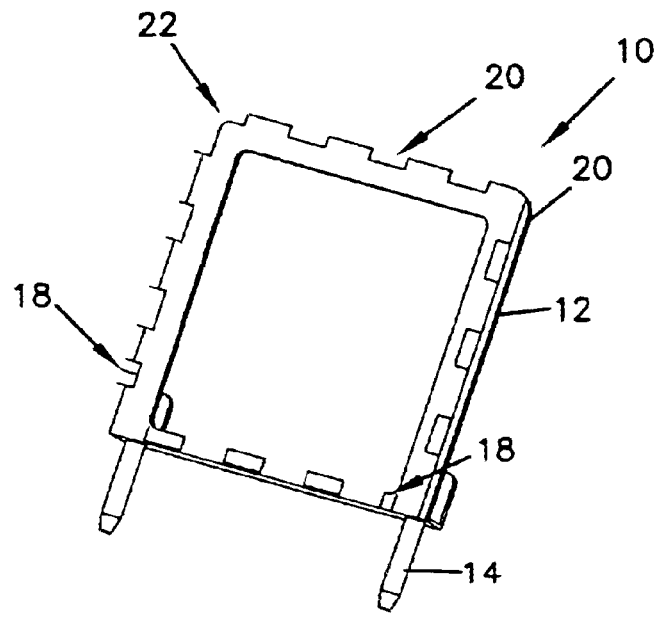
FIG. 1 shows a perspective view of one embodiment of a template grid according to the present invention.

As shown in FIG. 1, a template grid 10 according to the present invention includes a frame 12. Frame 12 is made of a material, such as aluminum, that can be sterilized and cleaned. Although frame 12 can be made to be disposable, in one embodiment, frame 12 is reusable. In this embodiment, frame 12 should be cleaned and sterilized before each use. Frame 12 can be provided with one or more prongs 14 extending from a lower surface to facilitate coupling with another instrument or a base. For example, prongs 14 can be used to mount template grid 10 to a stepper device.

Figure 2:
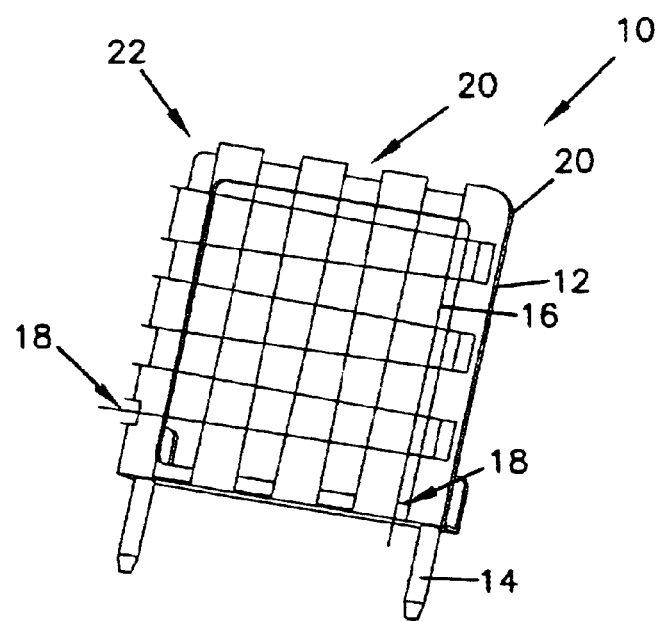
FIG. 2 shows the template grid of FIG. 1 with suture forming the grid.

At least one of the faces of frame 12 includes protrusions for coupling with suture 16 or similar material that forms a matrix or network (FIG. 2) that serves as the guidance mechanism. The first type of protrusion, cleat 18, is used to secure an end of suture 16 to frame 12. In one embodiment, this is achieved with resilient ends that are biased together to hold suture 16 via a friction fit, such as within a slot define by the resilient ends. Other type of holding mechanisms can be used. Two cleats 18 are provided on frame 12. One cleat 18 serves as the starting point of suture attachment and the other cleat 18 serves as the end point. Thus, the locations of cleat 18 can influence the grid formed by suture 16.

Tabs 20 are the second type of protrusions. Once suture 16 is lodged into one of the cleats 18, suture 16 is pulled across frame 12 and around one of tabs 20. This procedure is repeated so that if suture 16 is pulled with sufficient tension, a set of parallel lines is formed with suture 16. When one complete set of rows is completed, corner tab 20 includes a curved edge and facilitates a transition in suture direction. Specifically, suture 16 is pulled around corner tab 22 so that a second set of suture lines, perpendicular to the first set, can be formed. This is continued until the second cleat 18 is reached, at which point suture 16 is pulled firmly down into this cleat 18. After use, suture 16 maybe removed from frame 12 to allow sterilization of frame 12. Subsequently, a frame in accordance with the present invention may be re-used by forming thereon another grid of suture or similar material.

The first and second protrusions are examples of network supports for supporting or securing a wire network, such as one formed by suture 16, with respect to frame 12.

The present invention also encompasses frames that have types and/or arrangements of protrusions that differ from frame 12 as shown and described herein. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A medical device guide, comprising:

a frame comprising a plurality of network supports; and a wire network supported by the network supports, the wire network forming a plurality of meshes, whereby a medical device may be inserted through one of the meshes to guide the medical device:

wherein the wire network is formed by wrapping a wire around the frame to form a grid, said network being removable from the frame so as to be replaced by a new wire network wrapped around the frame.

2. The medical device guide of claim 1, wherein the medical device is a device for positioning a radioactive seed with respect to a prostate.

3. The medical device guide of claim 1, wherein the network supports comprise at least one slot for frictionably securing a wire of the wire network.

4. The medical device guide of claim 1, wherein a wire of the wire network is suture.

5. The medical device guide of claim 1, wherein the wire network may be removed from the frame and replaced with a second wire network.

* * * * *